United States Patent [19]

Chareire et al.

[11] Patent Number: 4,822,356

[45] Date of Patent: * Apr. 18, 1989

[54] EXTRA-PERICARDIAL MODULE FOR TOTAL CARDIAL PROSTHESIS MODULES ASSOCIATED IN A FUNCTIONALLY INDISSOCIABLE UNIT

[75] Inventors: Jean-Louis Chareire, Levallois; Didier Lapeyre, Pacy-sur-Eure, both of France

[73] Assignee: Aerospatiale Societe Nationale Industrielle, Paris, France

[*] Notice: The portion of the term of this patent subsequent to Nov. 18, 2003 has been disclaimed.

[21] Appl. No.: 942,074

[22] Filed: Dec. 15, 1986

[30] Foreign Application Priority Data

Dec. 13, 1985 [FR] France ............................... 85 18514

[51] Int. Cl.⁴ ............................................. A61F 2/22
[52] U.S. Cl. ........................................................ 623/3
[58] Field of Search .............................................. 623/3

[56] References Cited

U.S. PATENT DOCUMENTS

| | | | |
|---|---|---|---|
| 4,105,016 | 6/1978 | Donovan, Jr. ..................... | 128/1 D |
| 4,167,046 | 9/1979 | Portner ................................. | 3/1.7 |
| 4,195,623 | 4/1980 | Zeff et al. ........................... | 128/1 D |
| 4,457,673 | 7/1984 | Conley ..................... | 623/3 |
| 4,557,673 | 12/1985 | Chen ......................... | 623/3 |
| 4,565,497 | 1/1986 | Miller ....................... | 623/3 |
| 4,623,350 | 11/1986 | Lapeyoe et al. ......................... | 623/3 |
| 4,650,486 | 3/1987 | Chaveire ................................ | 623/3 |

FOREIGN PATENT DOCUMENTS

| | | |
|---|---|---|
| 0146445 | 7/1985 | European Pat. Off. . |
| 8318368 | 5/1985 | France . |
| 8518425 | 6/1987 | France . |

Primary Examiner—Richard J. Apley
Assistant Examiner—James Prizant
Attorney, Agent, or Firm—Fisher, Christen & Sabol

[57] ABSTRACT

Extra-pericardial module for total cardinal prosthesis with two pumps joined together by a functional link. The extra-pericardial module comprises a rigid casing, inside which two pushing plates are disposed. The pushing plates are facing each other and divide the inside of the casing into an inner pumping cavity and into two peripheral chambers inside which are disposed the actuation devices for pushing plates. Thus, it is obtained a single unit comprising, inside of the casing, the pushing plates and their actuators.

10 Claims, 7 Drawing Sheets

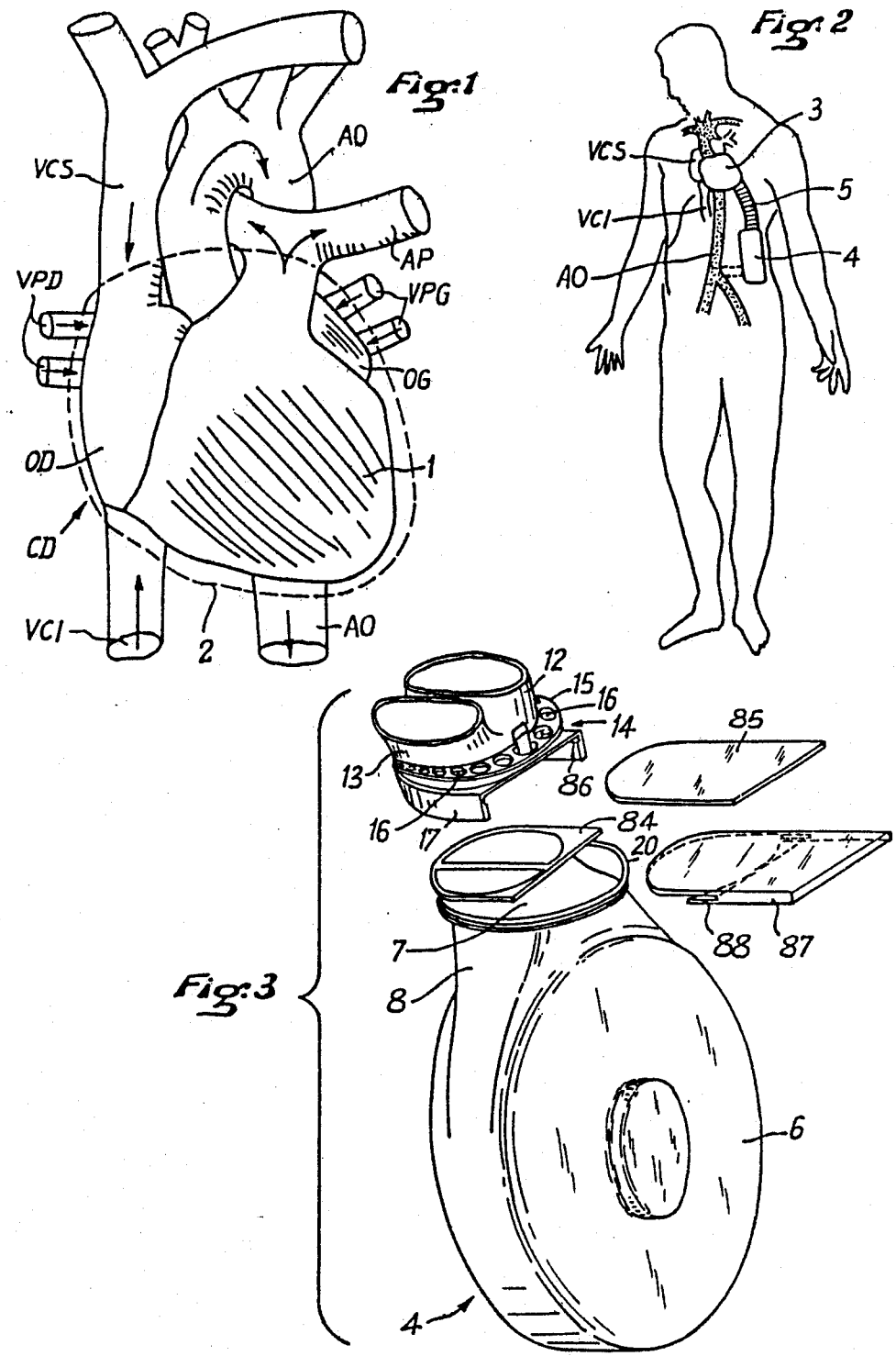

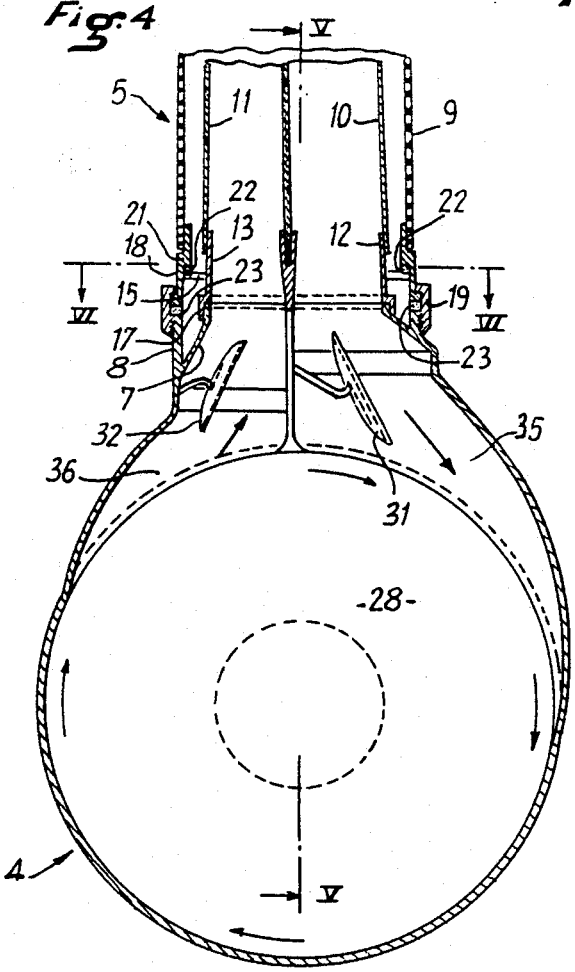
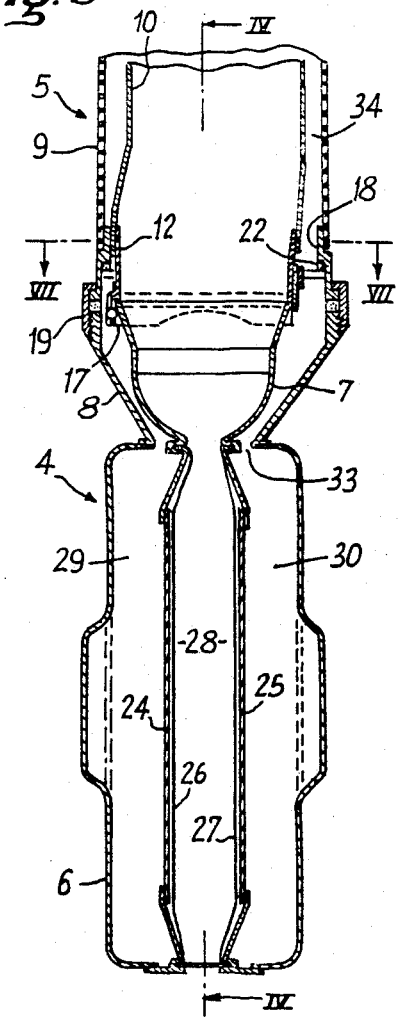
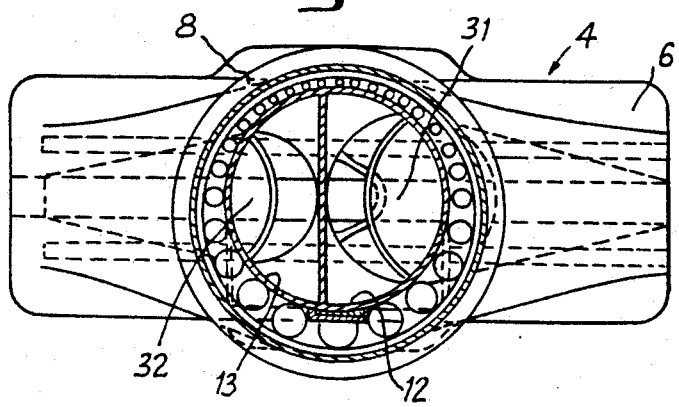
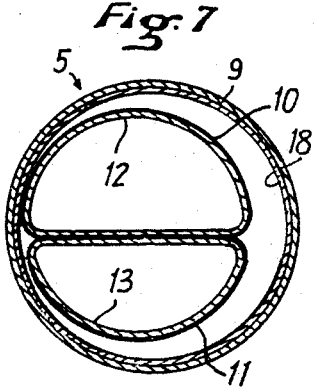

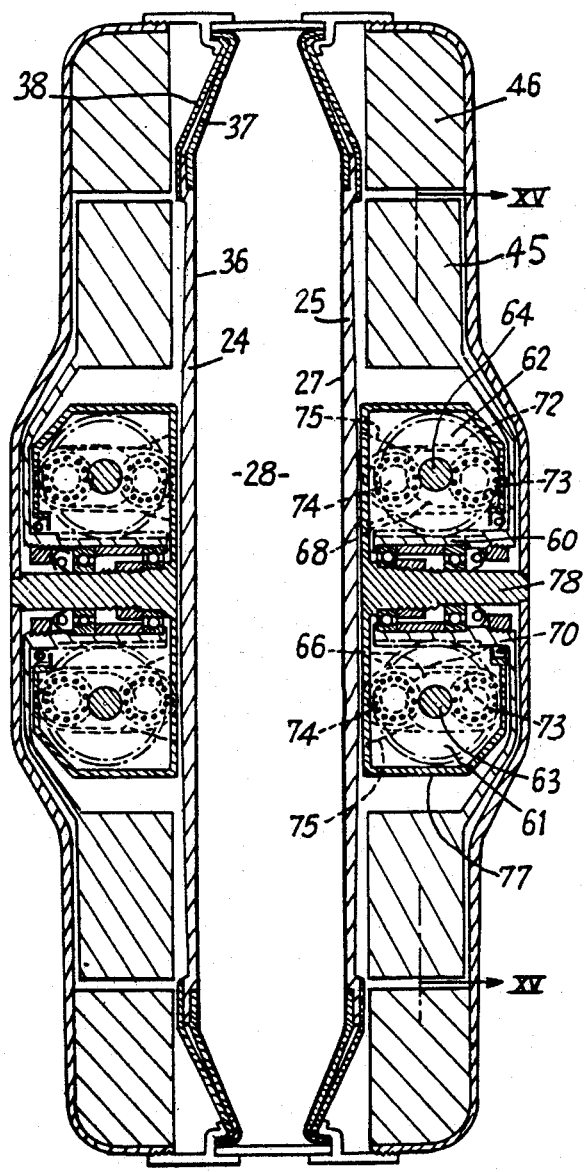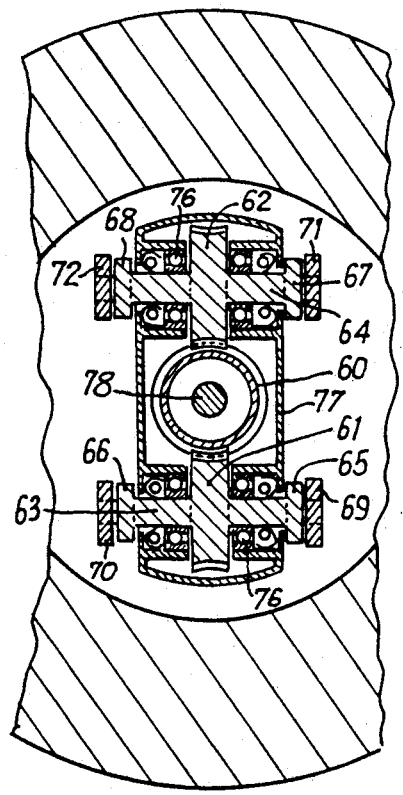

EXTRA-PERICARDIAL MODULE FOR TOTAL CARDIAL PROSTHESIS MODULES ASSOCIATED IN A FUNCTIONALLY INDISSOCIABLE UNIT

French Patent Applications No. 83 18368 filed on Nov. 18, 1983, (also see U.S. Pat. No. 4,623,350), and No. 85 18425 filed on Dec. 12, 1985, which respectively correspond to U.S. Ser. No. 672,376, filed on Nov. 16, 1984, and U.S. Ser. No. 941,0446, filed on Dec. 12, 1986, describe two embodiments of a total cardial prosthesis comprising two pumps, respectively representative of the right heart and of the left heart, as well as a device for controlling said pump, said prosthesis being noteworthy in that, on the one hand, it comprises the indissociable functional unit constituted by:

a pericardial module adapted to be housed in the cavity of the natural heart to be replaced and enclosed in a tight envelope comprising at least three orifices for connection adapted respectively to be connected to the right atrium, to the pulmonary artery, and to the left atrium, said orifices for connection to the right atrium and to the pulmonary artery being provided with valves in order to serve respectively as input orifice and as output orifice for a first pump housed in said pericardial module and adapted to perform the function of the right heart of the natural heart to be replaced;

an extra-pericardial module adapted to be housed in a physiologically neutral space in the recipient patient and to perform the function of the left heart of the natural heart to be replaced, this extra-pericardial module comprising a tight envelope in which is enclosed a second pump provided with an input orifice and an output orifice, each provided with a valve;

a functional link between said pericardial and extra-pericardial modules comprising:

a first duct passing through the envelope of said pericardial module and connecting the orifice thereof corresponding to the left atrium and the input orifice of said second pump incorporated in said extra-pericardial module;

a second duct establishing a gaseous communication between the sides of said first and second pumps opposite the blood passing therethrough; and in that, on the other hand, said control device actuates said pumps in opposition.

In the first embodiment, the tight envelope of the pericardial module comprises a fourth orifice for connecttion with the aorta, and said functional link comprises a third duct passing through the envelope of said pericardial module and connecting said fourth orifice thereof corresponding to the aorta and the output orifice of said second pump incorporated in said extra-pericardial module.

In the second embodiment, on the contrary, the output orifice of said second pump incorporated in said extra-pericardial module is directly connected to the abdominal part of the aorta, which eliminates the need for the fourth orifice of the pericardial module and for said third duct of functional link.

In both these embodiments, the pericardial pumping and extra-pericardial modules are advantageously produced as diaphragm and thrust-plate pumps.

The object of the present invention is to describe particularly advantageous embodiments of extra-pericardial module for the aforementioned total cardial prosthesis.

To this end, according to the invention, the extra-pericardial module for a total cardial prosthesis comprising two pumps, respectively representative of the right heart and of the left heart and comprising the indissociable functional unit constituted of:

a pericardial module adapted to be housed in the cavity of the natural heart to be replaced and enclosed in a tight envelope comprising at least three orifices for connection adapted respectively to be connected to the right atrium, to the pulmonary artery, and to the left atrium, said orifices for connection to the right atrium and to the pulmonary artery being provided with valves in order to serve respectively as input orifice and as output orifice for a first pump housed in said envelope and adapted to perform the function of the right heart of the natural heart to be replaced;

an extra-pericardial module, adapted to be housed in a physiologically neutral space in the recipient patient and to perform the function of the left heart of the natural heart to be replaced, said extra-pericardial module comprising a second pump of the type with diaphragm and thrust plate enclosed in a tight envelope, provided with an input orifice and an output orifice, each equipped with a valve;

a functional link between said modules comprising at least:

a first duct passing through said envelope of said pericardial module and connecting the orifice thereof corresponding to the left atrium and the input orifice of the second pump incorporated in said extra-pericardial module;

a second duct establishing a gaseous communication between the sides of said first and second pumps opposite the blood passing therethrough; said first and second pumps being actuated in opposition, is noteworthy in that said second pump comprises, in its envelope, on the one hand, a tight enclosure which communicates with said input orifice and said output orifice of said second pump, and which is at least partly defined by two supple diaphragms, placed in facing relationship, and on the other hand, two thrust plates also in facing relationship, placed on either side of said tight enclosure in contact with a diaphragm and imparted with reciprocating back and forth movements under the action of mechanisms disposed respectively on the side of the corresponding thrust plate opposite said tight enclosure.

Thus, said second pump is really constituted of two pumping systems acting on the same deformable tight enclosure, so that, if one of said systems should break down, the pumping can continue under the action of the other.

When said first duct, and optionally a duct connecting the output orifice of said second pump and an orifice of the pericardial module connected to the aorta, are internal to said second conduit, the envelope of said second pump will advantageously be provided with an external neck for connection to said second conduit, and an internal neck for connection of each of said internal ducts, and passages will be provided, inside said envelope, between said necks, so that the parts of said envelope containing said mechanisms can communicate with the inside of said second duct.

Preferably, said extra-pericardial module is provided with a quick connection system permitting the simultaneous connection of said second duct and of each of said internal ducts with their respective necks.

According to an advantageous embodiment of the invention, said diaphragms are so arranged as to provide between them at least one peripheral channel when each one simultaneously take its maximum close-up position with respect to the other under the action of their respective mechanisms. Thus, the tight enclosure is traversed by a permanent flow of blood, which helps the pumping output and prevents the risks of thrombosis.

To this effect, each thrust plate may be at least approximately centered with respect to the corresponding diaphragm, and may cover the latter only partly, thus leaving between the inner wall of the envelope and it periphery, a free portion of diaphragm. The formation of said peripheral channel is further helped by the fact that the anchoring into the envelope of said peripheral portion of supple diaphragm is offset from the plane supporting said diaphragms, when the latter are in maximum close-up position.

In order to further improve the blood circulation inside said second pump, connection between said tight enclosure and each of said input and output orifices of said second pump is achieved by way of a shell.

It is moreover advantageous for said portion of supple diaphragm non-covered over by the corresponding thrust plate to be lined tightly by at least one ring in supple material. A tight space is thus defined between said ring and said diaphragm, inside which a sensor can be placed, which sensor is designed to detect a deterioration of said diaphragm, as soon as blood goes through it. It is likewise possible to provide at least another tight space between said ring and a next one, in order to follow the progression of a blood leak and therefore to control the state of operation of the pumping module.

The mechanisms actuating the thrust plates may be produced in different ways. For example, they may be of the stop-screw type. In this case, an electric motor with flat rotor and stator may be provided for each thrust plate, said motor actuating an axial screw acting on a nut integral with the thrust plate, which is prevented to turn thanks to its connection with the corresponding diaphragm. The two motors of the extra-pericardial module may have a reciprocating rotation movement and be in opposition so as to cancel any external torque.

A reduction gear may be provided between the rotor of the motor and the nut fixed to the thrust plate.

As a variant, the thrust plates may be actuated by connecting rod/crank systems fixed to a worm screw driven by an electric motor.

The invention will be more readily understood on reading the following description with reference to the accompanying drawings, in which:

FIG. 1 diagrammatically shows a natural heart together with its principal veins and arteries, in front view.

FIG. 2 diagrammatically shows a prosthesis of the type according to the invention, fitted in a patient.

FIG. 3 diagrammatically shows, in outside view with parts torn away, a first embodiment according to the invention of the extra-pericardial pumping module for total cardial prosthesis of the type referred to hereinabove, more specifically in the case where the aorta is connected to the pericardial module.

FIGS. 4, 5, 6 and 7 are cross-sections, respectively along lines IV—IV, V—V, VI—VI and VII—VII of the embodiment of the extra-pericardial module shown in FIG. 3, represented with part of its functional link to the pericardial module (not shown) of said prosthesis.

FIGS. 15 to 20 show different mechanisms for actuating the thrust plates of the extra-pericardial modules shown in FIGS. 3 to 12.

In these figures, like references designate like elements.

Figure 8:
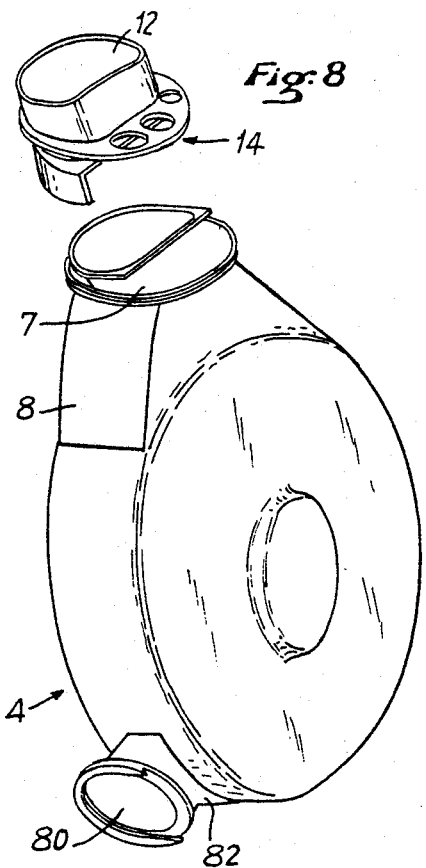
FIGS. 8 to 12 are diagrammatical views corresponding respectively to FIGS. 3 to 7, of a second embodiment according to the invention of the extra-pericardial module, more specifically in the case where the aorta is connected to said extra-pericardial module.

Referring now to the drawings, FIG. 1 shows a human heart 1 housed in the pericardial cavity 2 (simply illustrated by a broken line 2) and composed in fact of two hearts which are distinct from but fast with each other, namely the right heart CD comprising the right atrium OD and the right ventricle and the left heart CG comprising the left atrium OG and the left ventricle. The atrium OD of the right heart CD receives the venous blood through the superior vena cava VCS and through the inferior vena cava VCI, while the ventricle of said right heart CD passes the blood thus received towards the lungs via the pulmonary artery AP.

Similarly, the atrium OG of the left heart CG receives the blood coming from the lungs by the left pulmonary veins VPG and by the right pulmonary veins VPD and the ventricle of the left heart CG drives out the blood received by the aorta AO.

The gist of the prosthesis with uncoupled pumps of the type to which the present invention refers lies in the physiological observation that, although constituted by two pumps CD and CG forming a single muscular unit, the heart 1 is in fact composed of two functionally independent assemblies. Indeed, from the functional standpoint, the right heart CD may be considered as a simple heart of passage which pushes a column of blood of which the speed of flow is variable, but never zero, except when the frequencies of the beats of the heart 1 are very low. When the blood flowrate of the vascular system increases, further to an increase in frequency of these beats, the participation of the right heart CD in the movement of the blood in the pulmonary circuit decreases due to the increase in the speed, and therefore in the kinetic energy, of the blood arriving at the right heart CD. On the other hand, the left heart CG, by its powerful ventricle, constitutes the heart proper, i.e. the propelling pump ensuring perfusion of blood in all the organs and tissues of the organism.

Moreover, the gist of the invention is based on the fact, known to the man skilled in the art, that the contraction of the ventricle of the right heart CD and that of the ventricle of the left heart CG are not necessarily simultaneous, but in phase opposition.

As illustrated very diagrammatically in FIG. 2, said total cardial prosthesis is constituted by a functionally indissociable unit constituted by two pumping modules 3 and 4 which are uncoupled but connected to each other by a tubular functional link 5.

The pumping module 3, adapted to replace the right heart CD of the natural heart 1, is housed in the pericardial cavity 2. It comprises a tight envelope on which are mounted connecting unions of any known type, respectively intended to connect it to the right atrium OD (reservoir of the venae cavae VCI and VCS), to the pulmonary artery AP, to the left atrium OG (reservoir of the pulmonary veins VPG and VPD), and optionally to the aorta AO, after section thereof and excision of the natural ventricals from the pericardial cavity 2.

The orifices for connection to the right atrium OD and to the pulmonary artery AP are provided with valves serving respectively as input orifice and output orifice to a pump housed in said envelope and intended to perform the function of the right heart of the natural heart to be replaced.

The pumping module 4, intended to play the role of the left heart CG of the natural heart 1, is housed outside the pericardial cavity 2, inside a physiologically neutral space, such as the thorax or the abdomen. It further comprises a tight envelope enclosing a pump provided with an input orifice and an output orifice, each orifice being equipped with a valve.

The functional link 5, which may pass through the diaphragm of the patient recipient of the prosthesis, without any inconvenience, comprises:

a duct connecting the orifice of the pericardial module 3 corresponding to the left atrium OG and the input orifice of the pump incorporated in the extra-pericardial module 4;

optionally, when the output orifice of the pump of the extra-pericardial module is not directly connected to the abdominal aorta, a duct connecting the orifice of the pericardial module 3 corresponding to the aorta AO and the output orifice of said pump incorporated in said extra-pericardial module 4;

a duct establishing a gaseous communication between the sides of the pumps of the pericardial module and of the extra-pericardial module opposite the blood passing therethrough;

In addition, a control device (not shown) actuates the two pumps in opposition and controls the valves placed in said orifices.

FIG. 2 diagrammatically illustrates in dotted lines the fact that the output orifice of the pump of the extra-pericardial module 4 could be directly connected to the abdominal part of the aorta. In this case, the pericardial module 3 has no orifice of connection with the aorta and the link 5 only has two ducts.

Thus, the extra-pericardial module 4 of the total prosthesis of the type referred to hereinabove, is destined to replace the left heart of the natural heart to be replaced. It is therefore required to perform an important pumping work and to withstand the highest fatigue. Consequently, its pumping system must be particularly reliable, even if the extra-pericardial module 4 is disposed in a physiologically neutral space, such as the abdomen, easily accessible by a minor surgical operation, for ready replacement if the need arises. Due to the fact that said extra-pericardial module 4 is placed in a space which may be of large volume, the pumping system has not necessarily to follow critical dimensional servitudes, and can therefore reach very high standards of quality.

The embodiment of extra-pericardial module 4 shown in FIGS. 3 to 7 is destined for the first embodiment of prosthesis referred to hereinabove, in which the pericardial module 3 is connected to the aorta. It comprises an envelope or casing 6, shaped as a disc, enclosing the pumping mechanism (not shown in FIGS. 3 to 6) and provided with necks 7 and 8 for peripheral connection, which necks are fitted one into the other and have axes which are radial with respect to the envelope 6. A quick connection system can fasten onto the connection necks 7 and 8 for connecting the link 5 with the pericardial module 3. Said necks 7 and 8 are laterally connectable with the inner peripheral walls of the casing 6 via shells 35 and 36.

As illustrated in FIGS. 4, 5 an 7, said link 5 comprises an external tube 9, an artificial common pulmonary vein 10 and the artificial extension 11 of the aorta. The pulmonary vein 10 and the aorta 11 are surrounded and protected by the external tube 9. The pulmonary vein 10 is for example made of soft polyurethane, as explained in the patents referred to hereinabove, and plays the part of a complementary left atrium as well as that of adapting the gaseous pressures to the local atmospheric pressure, since it is in relation with the air pressure inside the lungs. In order to fulfill its function, the external tube 9 is rigid radially, but supple under bending stresses and longitudinally elastic. To this effect, it can be produced with a rigid wire spiral sheathed in supple elastomer.

The pulmonary vein 10 and the aorta 11 are respectively fixed on unions 12 and 13 of a part 14 which can be locked on the free end of the internal neck 7. Said part 14 which is part of the quick connection system for connecting the link 5 to the pericardial module 4, comprises a flange 15, perforated with holes 16, and a collar 17. Said unions 12 and 13, produced for example in titanium, are welded to the flange 15 and to the collar 17. They are advantageously coated internally with polyurethane or carbon deposited by vapor phase deposition.

The external tube 9 of the link 5 is secured to a sleeve 18 gripping in position a nut 19, adapted to cooperate with a threading 20 provided on the end of the external neck 8. Said sleeve 18 comprises a shoulder 21 against which rests the periphery of the flange 15, via an elastic ring 22. Another elastic ring 23 is provided between the sleeve 18 and the threading 20.

Thus, the tightening of the nut 19 simultaneously ensures the fastening of the external tube 9 on the external neck 8 and the fastening of the artificial pulmonary vein 10 and of the artificial aorta 11 on the internal neck 7. Indeed, when the nut 19 is screwed in the tightening direction, it applies the sleeve 18 against the free end of the external neck 8 and the collar 17 of the part 14 against the free end of the internal neck 7, tightness being then ensured by the joints 22 and 23.

Sleeve 18 and nut 19 may be produced in titanium or in stainless steel.

Two thrust plates 24 and 25, actuating diaphragms 26 and 27 respectively, are disposed inside the casing 6. Said thrust plates 24 and 25 are facing each other and are parallel to the median plane of the casing 6. They divide the inside of the casing 6 into an inner pumping cavity 28 and into two peripheral spaces 29 and 30 inside which are disposed the mechanisms (not shown in FIG. 5) actuating said thrust plates 24 and 25. Under the action of these mechanisms, the two thrust plates 24 and 25, can move close together or apart.

The inner cavity 28 may be caused to communicate with the pulmonary vein 10 and with the aorta 11, via valves 31 and 32, respectively. The peripheral spaces 29 and 30 are in gaseous communication (via passages 33) with the inner volume 34 of tube 9, non-occupied by the pulmonary vein 10 and the aorta 11, this being achieved via holes 16 of flange 15.

Figure 9:
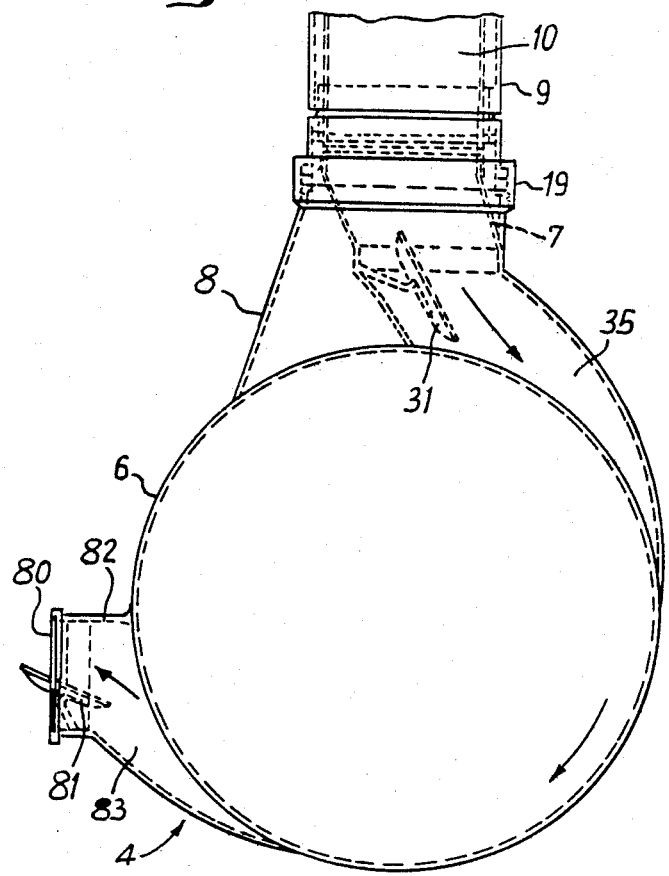
Figure 10:
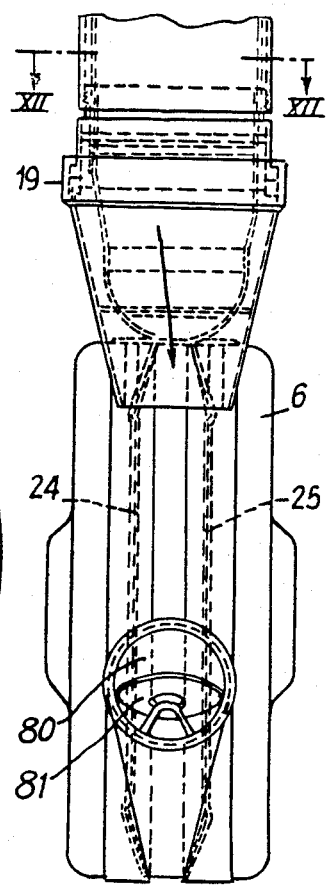
Figure 11:
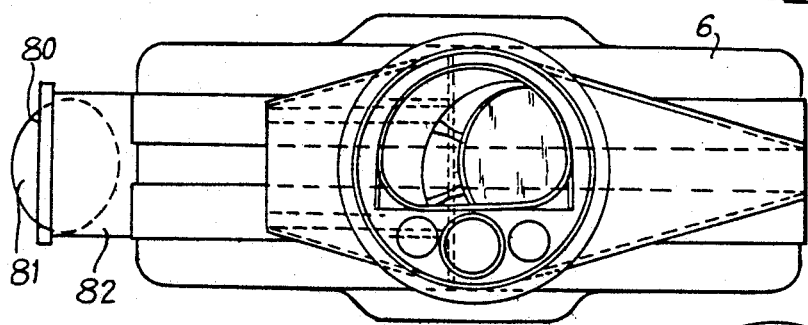
Figure 12:
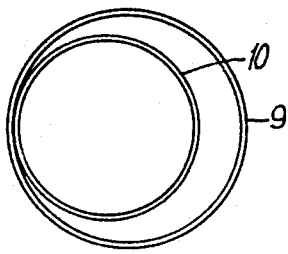

FIGS. 8 to 12 respectively show, in external perspective with parts torn away, in front view, in side view, in plan view, and in cross-section along line XII—XII of FIG. 10, one embodiment of an extra-pericardial module 4 according to the invention, for the prosthesis in which said module is directly connected with the abdominal part of the aorta. In this case the artificial aorta 11 is eliminated and only the pipe 10 is inside the external tube 9.

But then, there is provided a side orifice 80 which is equipped with a valve 81 and with a quick connection union 82 for connection to the abdominal part of the aorta. In this case, of course, a shell 83 may connect the orifice 80 with the inside of the casing 6.

On the whole, the modules of FIGS. 3 to 7, on the one hand, and those of FIGS. 8 to 12, on the other hand, are similar and include the same mechanisms and the same diaphragm devices.

As illustrated also in FIGS. 13, 14, 15, 16, 17 and 19, each thrust plate 24 or 25 is articulated on the inner wall of the casing 6 via a peripheral ring 37 in inextensible supple material, such as for example a natural or synthetic cloth coated with elastomer. The rings 37 are fast with the periphery of the thrust plates by their inner edge and fast with the casing 6 by their outer edge. The anchoring lines of the outer edges of the rings 37 along the inner wall of the casing are parallel and spaced apart. Thus, even when the two thrust plates of a module 4 nearly reach a position of contact against each other, the corresponding rings 37 provide between them a peripheral channel.

The two diaphragms 26 and 27 are made for example of supple polyurethane, in order to be haemocompatible. They cover entirely the thrust plates 24 and 25 and the corresponding articulation rings 37, on the side of the inner pumping cavity 28.

Figure 13:
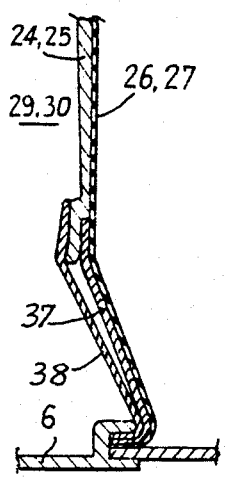
FIG. 13 shows, on an enlarged scale, the mounting of the thrust plates of the extra-pericardial module with respect to the casing thereof, for the two embodiments respectively shown by groups of FIGS. 3 to 7 and 8 to 12.

According to the embodiment illustrated in FIG. 13, articulation ring 37 is lined with a ring 38 disposed on the side of the corresponding peripheral space 29 or 30. This additional ring 38 has a safety function as will be seen hereinafter and enables a reduction of the pulling force exerted on the junction, which may be adhesive, between the ring 37 and the thrust plate 24, 25 when there is a gaseous pressure.

Figure 14:
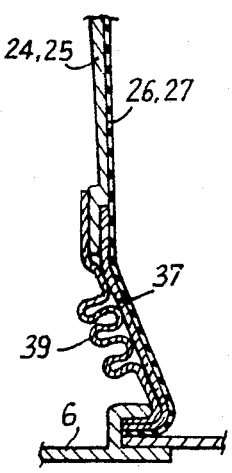
FIG. 14 shows a variant of the mounting of FIG. 13.

According to the variant illustrated in FIG. 14, the additional ring 38 is replaced by an elastic washer 39 provided with concentric plies and which can be made of steel, synthetic material, etc... Thanks to its plied structure, said elastic washer 39 suffers no great radial stresses, and its role is altogether to ensure a reliable tightness, to oppose delamination of the diaphragms 26,27 and to relieve the stresses to which the diaphragms and the rings 37 are subjected at their junction with the thrust plates 24, 25 and with the inner wall of the casing 6.

Thus, when the thrust plates 24 and 25 move apart from each other under the action of their respective mechanisms and when the admission valve 31 is open (position shown in FIGS. 4 and 9), the blood coming from the artificial vein 10 is sucked into the inner cavity 28 whose volume increases. To penetrate into the inner cavity 28, the blood passes through the distribution shell 35. Then, when the thrust plates 24 and 25 move closer together and when the discharge valve 32 or 81 opens (as illustrated in FIGS. 4 and 9), the blood which had been precedingly sucked into the inner cavity 28 is expelled into the artificial aorta 11, or towards the abdominal aorta, after passing through the output shell 36 or 83.

The shells 35, 36 and 83, the valves 31, 32 and 83 and other elements of the thrust-plate pump may be made of a biocompatible metal or alloy, such as titanium, stainless steel, vitallium, etc. . . . They may also be made of a non-biocompatible material, but then they must be coated with a biocompatible layer. These various elements are assembled for example by welding, by microplasma, electronic bombardment or laser.

During pumping, the thrust plates 24, 25 become nearly jointed, but they always maintain between them a gap of a few tenths of a millimeter for the blood. The conical deformation that they undergo due to the pressure enables, on the other hand, a better evacuation of the blood. Finally, a free toric volume is always left at the periphery of the thrust plates so that the blood can flow therethrough, permanently following a continuous swirling movement. The blood flowing direction (indicated by arrows in FIGS. 4 and 9) is always the same inside the pump, whether this pump is in filling or emptying position, due to the disposition of the input and output shells 35, 36 and 83. Thanks to that disposition, the hydraulic pumping output is very good and the risk of thrombosis is very small, since all the walls are actively swept by the permanent blood flow. And thanks to that symmetrical disposition, the diaphragms only move very little, hence a poor mechanical fatigue.

Examples of mechanical systems for actuating the thrust plates 24, 25 are given in FIGS. 15 to 20. The plates, the diaphragms and the shells are the same in all five examples described hereinafter.

In the first example (shown in FIG. 15), the system comprises, for each thrust plate 24 or 25, a screw 40 and a nut with a circulation of balls 41 integral with the plate. The circulation of balls takes place in the area of the nut 41 which remains in permanent engagement with the screw 40. The communication of the balls between the two serviceable ends of the nut is done through a duct 43.

The screw 40 turns about its axis thanks to a deep groove ball bearing 44 permitting an adequate geometrical marking. Finally, the screw 10 is connected to the rotor 45 of a flat electric motor of which the annular stator has the reference 46.

The axial displacement of a thrust plate 24, 25 is obtained by rotating the rotor 45, which causes the screw 40 to turn, said thrust plate being immobilized in rotation by diaphragms 26,27,37,38,39.

The screw with a circulation of balls and the bearing 44 are lubricated with an oil (for example) of viscosity just sufficient to allow it to flow very slowly when there is no driving pressure. Said lubricant (which only fills a small fraction of the available volume) is confined by the lip seal rings 46 and 47.

The system illustrated in FIG. 6 only, in order to simplify the drawings, is used to avoid that the pressures and depressions successively imposed on the lubricant, create leaks.

This system comprises a duct 48 cut through the thickness of the thrust plates 24, 25 and connecting a tube 49 with those parts of the pump which are not subjected to very high pressure differences and which never (bar accidents) contain any lubricant. Tube 49 encloses a spring 50 which presses against a ball-valve 51.

Thus, when the thrust plate 24,25 moves away from the center part of the pump (blood filling phase) and some gas is compressed in the volume of the screw confined by the seals 46 and 47, said gas can easily escape through the tube 49 and the duct 48, since the ball-valve 51 compresses the spring 50.

On the contrary, when the thrust plate 24, 25 moves closer to the center of the pump, hence closer to the opposite thrust plate, no gas can penetrate into the volume where the screw is situated, since the ball-valve 51 acts as a closed valve. The relative depression then created in the volume containing the screw helps the lubricant, which normally would have tried to pass through the sealing rings 46 and 47, to penetrate inside said volume.

In practice, the ball-valve 51 does not deliberately create a perfect tightness, so that the object of said system is to prevent the lubricant from exerting any excessive pressure from the inside to the outside, at the level of the sealing rings.

The lubricant never reaches the ball-valve 51, whatever the orientation of the pump, because, on the one hand, the volume of lubricant is small compared to the volume confined by the seals 46 and 47 and, on the other hand, the ball-valve is in the center of that volume; moreover, the external body of the tube 49 comprises two ribs 52 and the whole assembly is coated with a product which protects it against wetting by the lubricant.

The ball bearing 44 and the stator 46 are secured on the casing 6 which is produced in several parts to allow mounting. Said casing may be in biocompatible, material or it may be coated with a biocompatible layer, or be made of biocompatible plastic material, such as polycarbonate.

In either case, since the system does not need to be dismountable, great use is made of assemblies by laser or electronic bombardment welding, or by adhesive bondings. The drawings deliberately show a number of series of unnecessary threadings, for comprehension's sake.

Understandably, pumping of the blood is achieved thanks to a rotation of a finite number of revolutions of the rotor in one direction, followed by the same finite number of revolutions in the other direction.

Mechanical reactions external to the pump which could be due to the reciprocating movement of the rotors, are eliminated since the two rotors of the module 4 function in opposition.

A helical spring 53 is placed on the axis of each thrust plate 24, 25, in the center of the screw. Its role is to reduce the necessary power of the motor, since it compresses when the module is filling up (pumping power nearly zero) and extends when the module is emptying, thereby reducing the power required from the motor.

The two electric motors 45, 46 of the module 4 are controlled, on the one hand, at average speed (pumping rhythm) and, on the other hand, cyclically, to obtain the most physiological curve of pressure possible in the blood.

Figure 15:
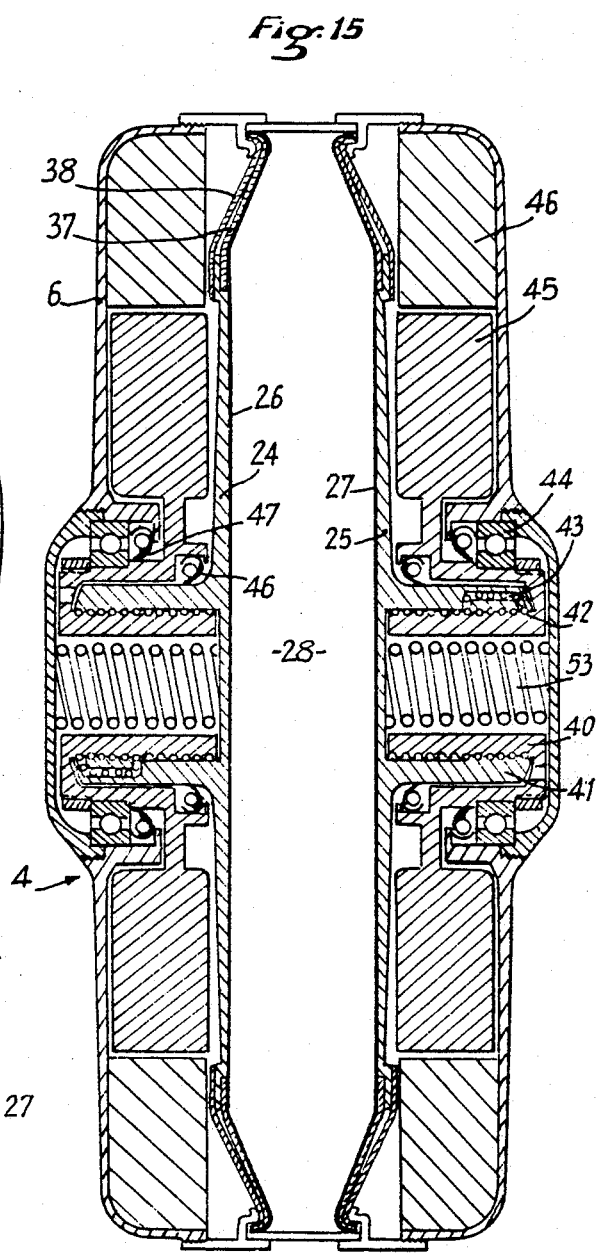
Figure 16:
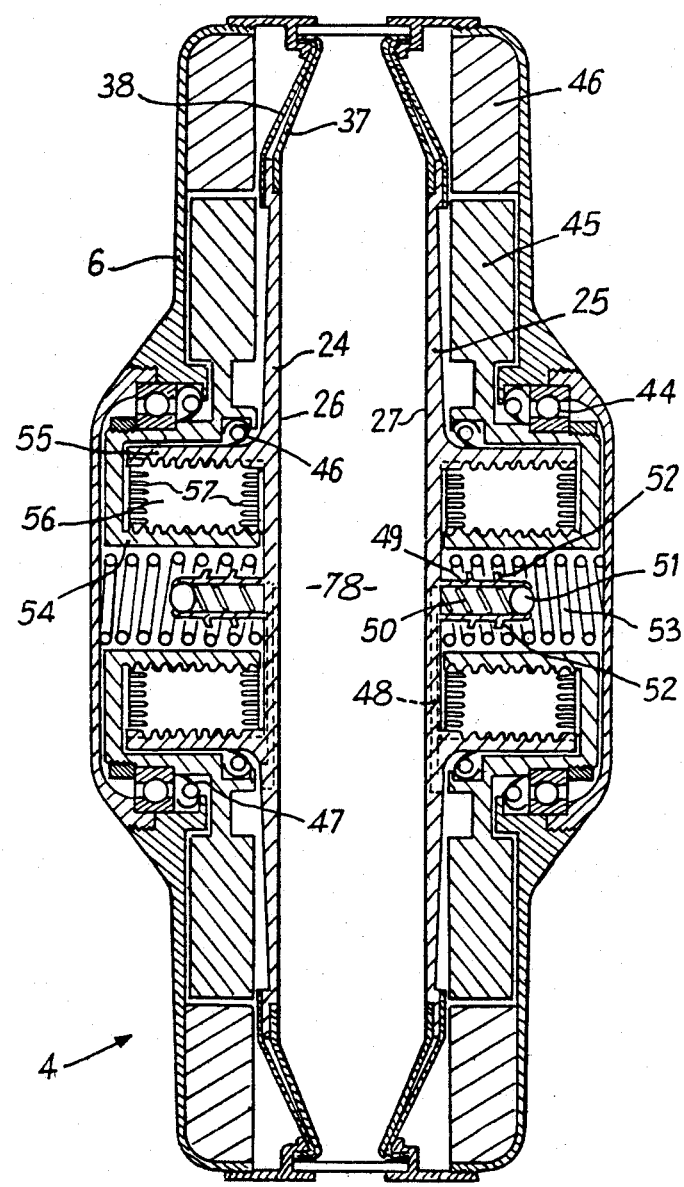

The actuating system illustrated in FIG. 16 is identical in every point to the system shown in FIG. 15, except for the screw 54, the nut 55 and the planet wheels 56, which form a helical bearing of the "TRANSROL" type.

The assembly composed of parts 54, 55 and 56 indeed constitutes a helical bearing/screw system. This technology is widely spread, particularly in aeronautics, and its object is mainly to obtain longer working lives than the working lives of ball-screws of identical load. However, it is used here in an original manner since its role is also to gear down the movement in order to be able to run the motors quicker than with the ball-screws and to reduce their overall dimensions and their weight.

Said assembly functions as follows:

The n threaded planet wheels 56 are provided at their two ends with gear teeth 57 which enable them to roll inside the nut 55 while remaining equidistant and parallel. The number of threads in the planet wheels 56 and in the nut 55 are determined so that there is no longitudinal displacement of the planet wheels with respect to the nut. The number of threads in the screw and their orientation are determined so as to have a small axial displacement of the screw with respect to the nut for every turn of the screw. The maximum axial displacement may thus require a much higher number of revs motor than in the case of ball-screws.

Figure 17:
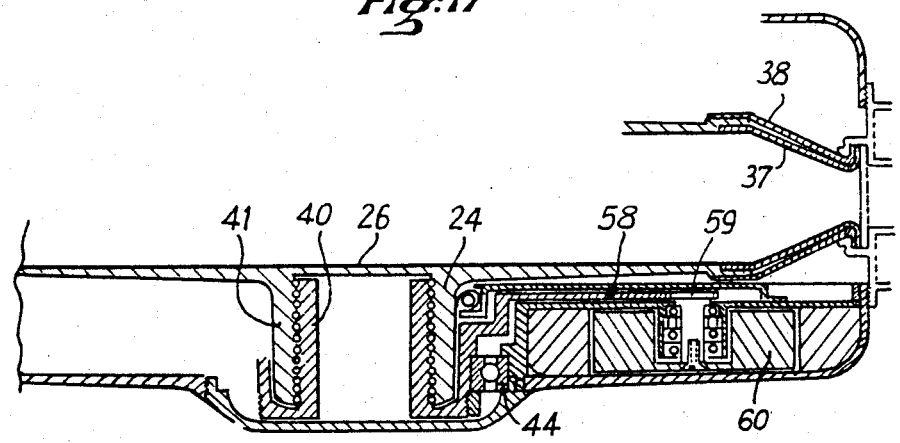
Figure 18:
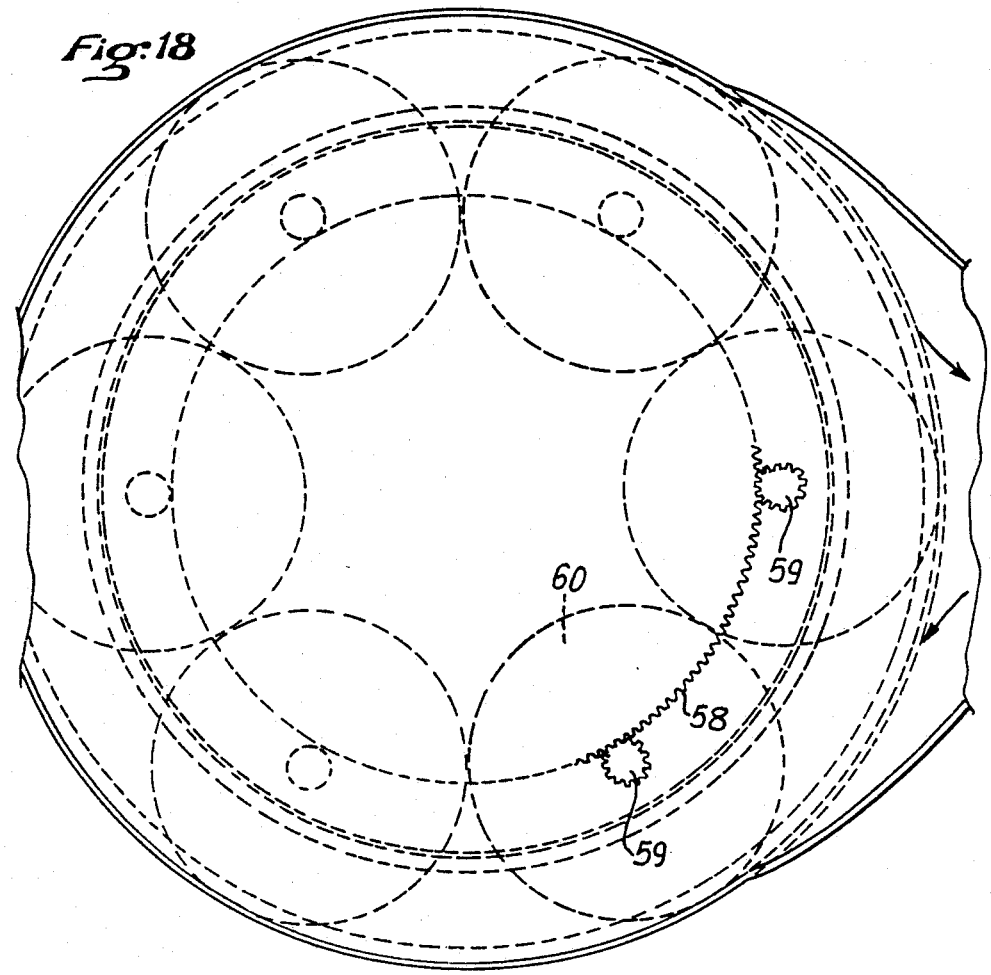

The actuating system diagrammatically illustrated in FIGS. 17 and 18 is identical to the system shown in FIG. 15 as far as the ball-screw is concerned. Said ball-screw, on the other hand, is not directly connected to the rotor of a motor.

It is fast with a gear wheel 58 actuated by a number of gear wheels 59 of very small diameter. These are connected to as many rotors 60 of small electric motors. This solution also makes it possible to use motors with high speeds of rotation.

The actuating system illustrated in FIGS. 19 and 20 differs from the three preceding ones by the fact that it uses two electric motors turning always in the same direction. The rotor 45 of each motor actuates a worm screw 60.

Said worm screw actuates two toothed wheels 61 and 62 which are locked in position on shafts 63 and 64, respectively.

Said shafts each drive two cranks: 65 and 66 for shaft 63, and 67 and 68 for shaft 64. Each one of these four cranks drives a connecting rod 69, 70, 71, 72 via a pin equipped with a ball bearing 73.

Finally, said four connecting rods transfer their load, through four other ball bearings 74, to four pins fixed on supports 75 fast with thrust plates 24, 25.

The assembly consisting of the worm screw 60, the two toothed wheels 61 and 62 and the four roller bearings 76 holding the shafts 63 and 64 in position is contained inside a tight enclosure 77 which is also used as a mechanical support for all the moving parts. Said enclosure 77 is, for example, in steel or in titanium, and is welded on the fixed pin 78, integral with the casing 6. All the mechanical forces involved in the actuating of the thrust plates 24, 25 are therefore supported by the pin 78, but in view of the symmetry of movement of the four connecting rod/crank systems, these forces are limited to pure traction or to pure compression with a slight torsional stress due to the action of the rotor 45.

The four actuating systems described hereinabove present the following advantages:

poor mechanical fatigue imposed on the diaphragms 25, 26 due to the shapes and very small displacements;

mechanical reliability due to the low level of stresses involved, to the possibility of preventing failures, to the permanent lubrication of all the moving parts and especially due to the possibility of one of the two pumping plates going out of action without any inconvenience other than that of increasing the rhythm of the other plate;

reliability of the diaphragms due to their respective disposition, to the possibility of preventing failures and to the possibility for one of the motors to stop if a leak is detected on the diaphragm in question;

comfort for the patient due to no mechanical reaction from the driving torques (except in the case where one of the motors has stopped, which only corresponds to a very temporary intervention), and due to relatively low speeds of rotation resulting in a very low level of noise;

possibility of a progressive start-up after the operation on the patient; the latter, being used to a low heart flowrate, should not see it increase suddenly. Thanks to the first three systems described hereinabove, it is easy to progressively increase the flowrate (independently of the rhythm) by acting on the stroke of the thrust plates, which stroke can be adjusted at discretion;

very good hydraulic output due to the permanent circular movement of the blood and to the position of the input and output shells;

very good resistance to thrombosis for the above reason;

easy fitting initially, and in particular easy replacement without the obligation of placing the patient under extra-corporeal blood circulation.

Failures can be prevented as follows:

(1) Deterioration of diaphragms.

Referring to FIGS. 13 and 14, it is clear that in order to arrive at a complete leak capable of flooding the back 29, 30 of the thrust plates 24, 25 and of making pumping impossible, the blood must go through three separate thicknesses:

the diaphragm 26,27 in haemocompatible polyurethane, the two rings 37,38 (or 39).

The security consists in detecting the leaks between the diaphragms 26,27 and the ring 37 and between the ring 37 and the ring 38 (or 39).

The detection can be carried out by measuring the hygrometry or the electric conductivity of the medium (the blood being an electrolyte), or by detecting special chemical elements of the blood, etc. . . .

The detection will therefore be made well before the sharp break between the thrust plates and the casing.

If a leak is detected between the diaphragm 26 or 27 and the ring 37, an alarm signal will be initiated which will urge the patient to undergo a precise technical examination as soon as possible.

If a leak is detected between the diaphragm 26 or 27 and the ring 37, as well as between the ring 37 and the ring 38 (or 39) simultaneously, the motor concerned will stop so that the leak cannot become more serious.

If, in an exceptional case, a complete breakdown of the diaphragm 24,25 should occur when the rings 37 and 38 (or 39) are already broken, the consequences would not really be serious as the motor would stop automatically: indeed, the blood circulation between the different diaphragms would lead, without a pumping movement, to a rapid thrombosis of the blood which would stop the leaks.

The use of the aforesaid precautions will therefore give a nearly-absolute guarantee of survival for the patient in the event of a diaphragm becoming faulty, provided that the second group of diaphragms does not breakdown during the replacement intervention.

(2) Mechanical failures

Serious mechanical failures such as jamming of the ball bearings for example cause excess currents which can put the motor in question out of service without affecting the pumping possibilities of the apparatus until its replacement within a period of several days to several weeks.

Less serious failures such as, for example, the breaking of only one of the four connecting rods of the system of FIGS. 19 and 20 can be detected by the microprocessor controlling the prosthesis and which will permanently compare the functioning of the two groups actuating the thrust plates. Any dissymmetry which is noted will start off the alarm signal.

Also, since the most probable failure is the lubricant leak, special precautions are taken to this effect:

the lubricant is in small quantity with respect to the total gaseous free volume, it does not chemically attack the pumping diaphragms, it is not electrically-conducting, it has a chemical marker which makes it possible to detect its presence in those areas where it should not be and to start off an alarm signal.

Numerous organic substances or silicones can therefore be suitable.

The following is a description of the initial installation and/or replacement method for the extra-pericardial module 4 using devices for draining out the air in the blood ducts.

According to FIG. 3, the collar 17 of the part 14 is designed to receive the upper flange 84 of neck 7 which fits therein.

The patient being in the lying down position, the axis of the pump is vertical and the top of the U formed by the walls of the collar 17 is facing upwards.

Consequently, as the flange 84 fits therein with precision (over its perimeter), it determines between itself and the collar 17, a tight volume, even when it is not applied against the bottom.

A transparent plate 85 is fitted in the groove 86 and closes off the blood ducts 12 and 13.

Another transparent plate 87 is fitted in the flange 84 thanks to its groove 88. The surface of the flange 84 is moreover coated with a slightly adhesive substance (such as thick grease for example) permitting the sliding of the plate 87, yet tending to prevent its rising.

Therefore, when the plates 85 and 87 are fitted into place, it is still possible to insert the flange 84 into the collar 17, and if the plates 85 and 87 come into contact with each other, there is no longer any air inside the U-shaped interval defined by the parts 17 and 84. Consequently, if the blood pump and the tubes 12 and 13 are respectively filled with blood and closed off by plates 85 and 87 (the transparency of said plates enabling a control of the absence of air bubbles), the fact of lifting plates 85 and 87 vertically cannot introduce any air into the blood circuit. It suffices then to bring the flange 84 closer to the collar 17 by a thickness equal to the sum of the thicknesses of plates 85 and 87.

What is claimed is:

1. Extra-pericardial module for a total cardial prosthesis comprising two pumps, respectively representative of the right heart and the left heart and comprising the indissociable functional unit constituted of:

a pericardial module adapted to be housed in the cavity of the natural heart to be replaced and enclosed in a tight envelope comprising at least three orifices for connection, adapted respectively to be connected to the right atrium, to the pulmonary artery, and to the left atrium, said orifices for connection to the right atrium and to the pulmonary artery being provided with valves in order to serve respectively as input orifice and as output orifice for a first pump housed in said envelope and adapted to perform the function of the right heart of the natural heart to be replaced;

an extra-pericardial module, adapted to be housed in a physiologically neutral space in the recipient patient and to perform the function of the left heart of the natural heart to be replaced, said extra-pericardial module comprising a second pump of the type with diaphragm and thrust plate enclosed in a tight envelope, provided with an input orifice and an output orifice, each equipped with a valve;

a functional link between said modules comprising at least:

a first duct passing through said envelope of said pericardial module and connecting the orifice thereof corresponding to the left atrium and the input orifice of the second pump incorporated in said extra-pericardial module;

a second duct establishing a gaseous communication between the sides of said first and second pumps opposite the blood passing therethrough; passages being provided inside of said envelope so that the parts of the envelope containing the mechanisms can communicate with the inside of said second duct, said first and second pumps being actuated in opposition, wherein said second pump comprises in its envelope, a tight enclosure which communicates with said input orifice and said output orifice of said second pump, and which is at least partly defined by two supple diaphragms, placed in facing relationship, and two thrust plates also in facing relationship, placed on either side of said tight enclosure in contact with a diaphragm and imparted with reciprocating back and forth movements, under the action of mechanisms disposed respectively on the side of the corresponding thrust plate opposite said tight enclosure.

2. Extra-pericardial module as claimed in claim 1, in which said first duct, and optionally a duct connecting the output orifice of said second pump and an orifice of the pericardial module connected to the aorta, are internal to said second duct, wherein the envelope of said second pump is provided with an external neck for connection to said second duct, and an internal neck for connection of each of said first and optional ducts, and said passages are provided between said necks.

3. Extra-pericardial module as claimed in claim 2, wherein said module is provided with a quick connection system for simultaneous connection of said second duct and of each of said internal ducts with their respective necks.

4. Extra-pericardial module as claimed in claim 1, wherein said diaphragms are so arranged as to provide between them at least one peripheral channel when each one simultaneously take its maximum close-up position with respect to the other under the action of their respective mechanisms.

5. Extra-pericardial module as claimed in claim 4, wherein each thrust plate is at least approximately centered with respect to the corresponding diaphragm and covers the latter only partly, thus leaving a free portion of diaphragm between the inner wall of the envelope and its periphery.

6. Extra-pericardial module as claimed in claim 5, wherein the anchoring into the envelope of said peripheral portion of supple diaphragm is offset from the plane supporting said diaphragms, when the latter are in maximum close-up position.

7. Extra-pericardial module as claimed in claim 1, wherein the connection between said tight enclosure and each of said input and output orifices of said second pump is achieved by way of a shell.

8. Extra-pericardial module as claimed in claim 5, wherein said peripheral portion of supple diaphragm uncovered by the corresponding thrust plate is tightly lined by at least one supple ring.

9. Extra-pericardial module as claimed in claim 1, wherein said mechanisms for actuating the thrust plates are of the screw and nut type, locked in rotation.

10. Extra-pericardial module as claimed in claim 1, wherein said mechanisms for actuating the thrust plates are of the connecting rod type.

* * * * *